(12) United States Patent
Hafner

(10) Patent No.: US 8,006,839 B2
(45) Date of Patent: Aug. 30, 2011

(54) METHOD AND APPARATUS FOR PACKAGING MEDICAL DEVICES

(75) Inventor: Michael Hafner, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 12/331,016

(22) Filed: Dec. 9, 2008

(65) Prior Publication Data

US 2010/0140124 A1 Jun. 10, 2010

(51) Int. Cl.
*B65B 7/16* (2006.01)

(52) U.S. Cl. ............... 206/363; 206/438; 206/524.8; 206/499

(58) Field of Classification Search .......... 206/438, 206/363, 439, 524.8, 499, 210, 514; 220/23.89, 220/23.88, 23.86, 23.83, 507
See application file for complete search history.

(56) References Cited

U.S. PATENT DOCUMENTS

| | | | |
|---|---|---|---|
| 2,678,143 A * | 5/1954 | Dillingham et al. .......... 206/509 |
| 3,013,656 A | 12/1961 | Murphy | |
| 3,463,353 A * | 8/1969 | Peebles .......... 206/514 |
| 4,211,325 A | 7/1980 | Wright | |
| 4,216,860 A | 8/1980 | Heimann | |
| 4,340,138 A * | 7/1982 | Bernhardt .......... 206/216 |
| 4,348,421 A * | 9/1982 | Sakakibara et al. .......... 426/394 |
| 4,697,703 A * | 10/1987 | Will .......... 206/438 |
| 4,730,726 A | 3/1988 | Holzwarth | |
| 4,736,850 A * | 4/1988 | Bowman et al. .......... 206/570 |
| 4,750,619 A | 6/1988 | Cohen et al. | |
| 4,959,071 A | 9/1990 | Brown et al. | |
| 5,040,681 A * | 8/1991 | Grusin .......... 206/503 |
| 5,090,571 A | 2/1992 | Walker | |
| 5,099,998 A * | 3/1992 | Curzon et al. .......... 206/514 |
| 5,117,979 A * | 6/1992 | Brightbill .......... 206/372 |
| 5,148,920 A | 9/1992 | Walker | |
| 5,423,828 A * | 6/1995 | Benson .......... 606/102 |
| 5,575,401 A * | 11/1996 | Trower et al. .......... 220/522 |
| 5,669,501 A | 9/1997 | Hissong et al. | |
| 5,669,506 A | 9/1997 | Lofgren et al. | |
| 5,720,391 A | 2/1998 | Dohm et al. | |
| 5,823,342 A | 10/1998 | Caudillo et al. | |
| 5,868,253 A | 2/1999 | Krueger et al. | |
| 6,059,111 A | 5/2000 | Davila et al. | |
| 6,199,696 B1 | 3/2001 | Lytle et al. | |
| 6,488,684 B2 * | 12/2002 | Sterghos et al. .......... 606/62 |
| 6,561,805 B2 | 5/2003 | Kumar | |
| 6,830,149 B2 | 12/2004 | Merboth et al. | |
| 6,976,584 B2 | 12/2005 | Maiola et al. | |
| 7,648,030 B2 | 1/2010 | Landis | |
| 2002/0120328 A1 | 8/2002 | Pathak et al. | |
| 2004/0112781 A1 | 6/2004 | Hofverberg et al. | |

(Continued)

*Primary Examiner* — J. Gregory Pickett
*Assistant Examiner* — King M Chu
(74) *Attorney, Agent, or Firm* — Baker & Daniels LLP

(57) ABSTRACT

In one exemplary embodiment, the present invention provides a container system having an outer shell defining a cavity that is configured to receive a first medical device component therein. A support tray is sized for receipt within the outer shell of the container system and is supported above the first medical device component. In one exemplary embodiment, the support tray defines a second cavity that may receive a second medical device component. In addition, a retention tray may be positioned within the cavity of the support tray and supported above the second medical device component. The retention tray facilitates the retention of the support tray within the outer shell and also facilitates the retention of the first and second medical device components in their desired positions within the container system. Additionally, positioned to extend across an opening in the outer shell is a cover.

26 Claims, 6 Drawing Sheets

U.S. PATENT DOCUMENTS

| | | |
|---|---|---|
| 2005/0023166 A1 | 2/2005 | Howlett et al. |
| 2005/0051549 A1* | 3/2005 | Nelson ........................ 220/23.83 |
| 2005/0268573 A1* | 12/2005 | Yan ................................. 53/425 |
| 2007/0034538 A1 | 2/2007 | Landis |
| 2007/0074989 A1* | 4/2007 | Merboth et al. .............. 206/438 |
| 2008/0073233 A1 | 3/2008 | Landis |

* cited by examiner

FIG_1

FIG_5

METHOD AND APPARATUS FOR PACKAGING MEDICAL DEVICES

BACKGROUND

1. Field of the Invention

The present invention relates to packaging for medical devices and, particularly, to methods and apparatuses for packaging medical devices.

2. Description of the Related Art

Medical devices that are designed for implantation into the human body, once manufactured, must be maintained in a sterile environment. Thus, in order to provide a medical device intended for implantation, sterile packaging that maintains the sterility of the medical device is used. Specifically, the medical device may be placed within the packaging and the packaging sealed. Then, the packaging is subjected to a sterilization process with the medical device sealed within the packaging.

In addition to maintaining the sterility of a medical device, medical device packaging must also protect the medical device from damage during transportation and delivery. To this end, various packaging designs have been utilized that immobilize the medical device within the packaging. Additionally, as certain medical devices are modular, i.e., they contain numerous, individual components that are combined by the surgeon to form a complete, implantable medical device, a separate, sterile package may be required for each individual component of the medical device. This increases the expense of inventorying the components of a medical device and also increases the time needed for and the cost of obtaining regulatory approval for each of the individual package designs.

SUMMARY

The present invention provides methods and apparatuses for packaging medical devices. In one exemplary embodiment, the present invention provides a container system having an outer shell defining a cavity that is configured to receive a first medical device component therein. An opening in the outer shell provides access to the cavity. A support tray is sized for receipt within the outer shell of the container system and is supported above the first medical device component. In one exemplary embodiment, the support tray defines a second cavity that may receive a second medical device component. In addition, a retention tray may be positioned within the cavity of the support tray and supported above the second medical device component. The retention tray facilitates the retention of the support tray within the outer shell and also facilitates the retention of the first and second medical device components in their desired positions within the container system. Additionally, positioned to extend across the opening in the outer shell is a cover. In one exemplary embodiment, the cover is formed from a material that is impermeable to oxygen. Advantageously, the cover provides a barrier to the passage of dirt and/or debris into the cavity of the outer shell and helps to maintain the sterility of the container system, as well as the medical device components contained therein.

In one exemplary embodiment, the outer shell of the container system includes a rim portion having an internal securement surface that is configured to mate with a corresponding resiliently deformable portion of the support tray. In this manner, the support tray may be snap-fit or otherwise interference fit to the outer shell. Similar to the outer shell, the support tray may also include an internal securement surface that is configured to contact a resiliently deformable portion of the retention tray when the retention tray is positioned within the cavity of the support tray. In this manner, the retention tray may be snap-fit or otherwise interference fit to the support tray. In addition, the snap-fit or interference fit of the retention tray to the support tray further strengthens the securement of the support tray to the outer shell by providing the additional biasing of the resiliently deformable portion of the support tray against the internal securement surface of the outer shell.

In another exemplary embodiment, the outer shell of the container system includes an internal shoulder that cooperates with an internal shoulder of the support tray to suspend the support tray at a distance spaced from a shell floor of the outer shell. Additionally, in this embodiment, the retention tray may also include a shoulder designed to correspond to and cooperate with the internal shoulder of the support tray. Thus, with the shoulders of the retention tray and the support tray engaged with one another, the retention tray is also suspended within the cavity of the outer shell at a distance spaced from the shell floor of the outer shell.

Advantageously, by providing an outer shell and a support tray, each of which define a cavity that is configured to receive a medical device component therein, multiple medical device components may be packaged together. This decreases the cost of shipping the medical device components by eliminating the need to send the components in separate packages. Additionally, the cost of stocking and inventorying the separate medical device components is also decreased. Further, because the container system of the present invention separates the different medical device components from one another within the cavity of the outer shell, inadvertent or other undesirable contact between the medical device components is prevented.

In one form thereof, the present invention provides a container system configured for containment of a sterile medical device component, the container system including: an outer shell having a shell floor and an outer shell wall extending from the shell floor, the shell floor and the outer shell wall cooperating to define a first cavity, the first cavity sized to receive at least a first medical device component therein, the outer shell wall having a rim portion defining an opening in the outer shell, the rim portion having an outwardly extending flange and a first internal securement surface; a support tray having a support floor and a support tray wall extending from the support floor, the support floor and the support tray wall cooperating to define a second cavity, the cavity sized to receive at least a second medical device component therein, the support tray wall having a first resiliently deformable portion defining a second internal securement surface, the support tray sized for receipt within the first cavity, wherein, with the support tray received within the first cavity, the first resiliently deformable portion interacts with the first internal securement surface to secure the support tray to the outer shell and suspend the support floor of the support tray within the first cavity at a distance spaced from the shell floor of the outer shell; and a retention tray having a tray floor and a retention tray wall extending from the tray floor, the retention tray wall defining a second resiliently deformable portion, the retention tray sized for receipt within the second cavity, wherein, with the retention tray received within the second cavity, the second resiliently deformable portion interacts with the second internal securement surface to secure the retention tray to the support tray and the outer shell.

In another form thereof, the present invention provides a container system for the receipt of medical device components, the system including: an outer shell having a shell floor and an outer shell wall extending from the shell floor, the shell floor and the outer shell wall cooperating to define a first cavity, the outer shell wall having a rim portion defining an opening in the outer shell, the rim portion having an outwardly extending flange and an outer shell internal shoulder; a first medical device component positioned within the first cavity; a support tray having a support floor and a support tray wall extending from the support floor, the support floor and the support tray wall cooperating to define a second cavity, the support tray wall defining a support tray shoulder, the support tray sized for receipt within the first cavity, wherein, with the support tray received within the first cavity, the support tray shoulder abuts the outer shell internal shoulder to suspend the support floor of the support tray within the first cavity at a distance spaced from the shell floor of the outer shell; a second medical device component positioned within the second cavity; a retention tray having a tray floor and a retention tray wall extending from the tray floor, the retention tray wall defining a retention tray shoulder, the retention tray sized for receipt within the second cavity, wherein, with the retention tray received within the second cavity, the retention tray shoulder abuts the support tray shoulder to suspend the retention tray within the first cavity at a distance spaced from the shell floor of the outer shell; and a cover secured to the outwardly extending flange of the outer shell, wherein the cover seals the first cavity.

In yet another form thereof, the present invention provides a method of packaging medical device components, the method including the steps of: providing a first medical device component; positioning the first medical device component in a first cavity defined by an outer shell by advancing the first medical device component through an opening defined in the outer shell; securing a support tray within the first cavity; positioning a second medical device component within a second cavity defined by the support tray; securing a retention tray within the second cavity; and securing a cover across the opening in the outer shell.

BRIEF DESCRIPTION OF THE DRAWINGS

The above-mentioned and other features and advantages of the present invention, and the manner of attaining them, will become more apparent and the invention itself will be better understood by reference to the following description of an embodiment of the invention taken in conjunction with the accompanying drawings, wherein.

Corresponding reference characters indicate corresponding parts throughout the several views. The exemplification set out herein illustrates one exemplary embodiment of the invention, in one form, and such exemplification is not to be construed as limiting the scope of the invention in any manner.

DETAILED DESCRIPTION

Figure 1:
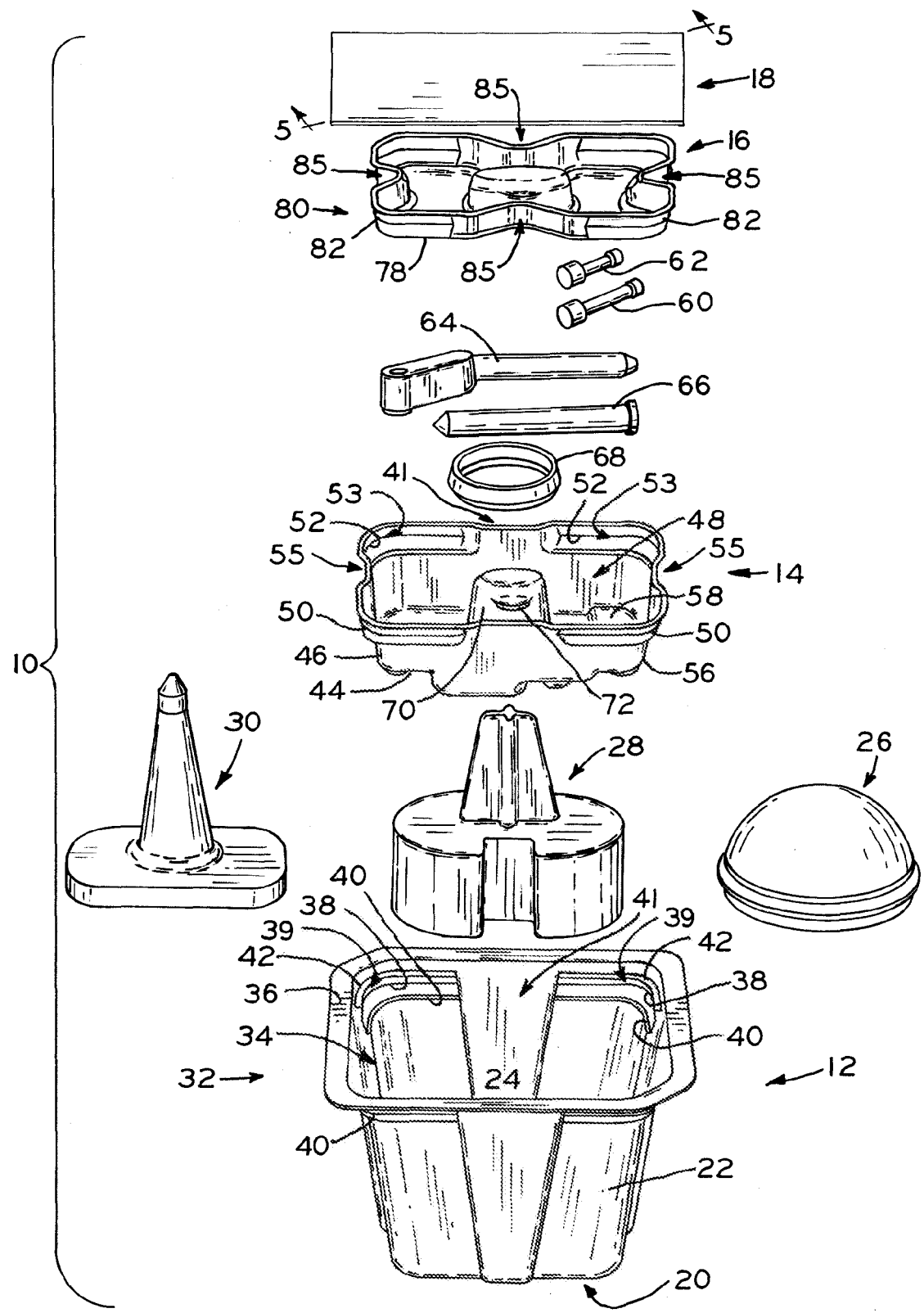
FIG. 1 is an exploded, perspective view of the container system of the present invention including exemplary medical device components that may be contained therein.
Figure 4:
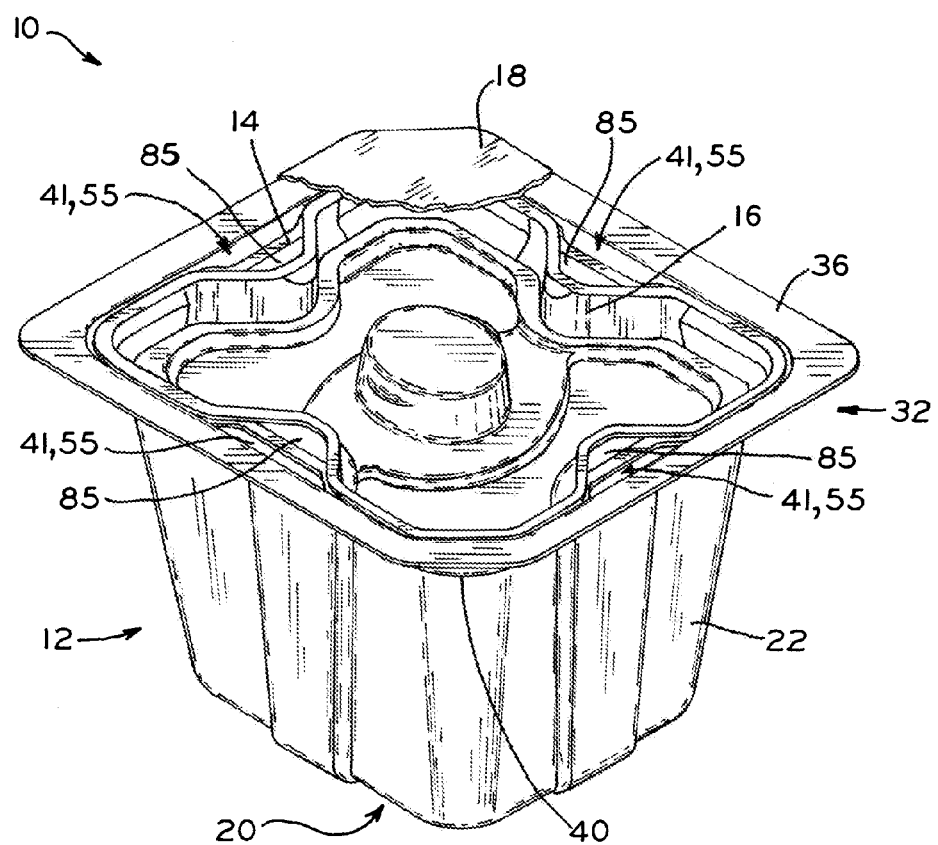
FIG. 4 is a fragmentary, perspective view of the container system of FIG. 1 in an assembled condition.
Figure 7:
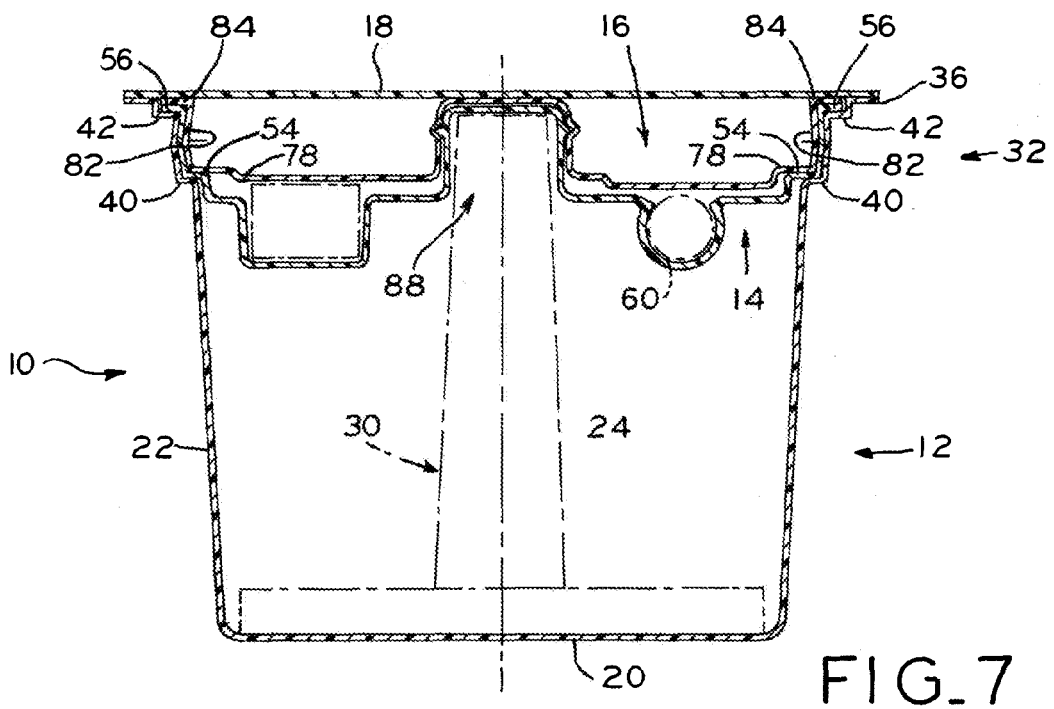
FIG. 7 is a cross-sectional view of the container system of FIG. 5 in an assembled condition.

Referring to FIG. 1, container system 10 is shown including outer shell 12, support tray 14, retention tray 16, and cover 18, which may be secured together, as shown in FIGS. 4 and 7, for the packaging of medical device components. Referring to FIG. 1, outer shell 12 includes shell floor 20 and wall 22 extending upwardly from shell floor 20. Shell floor 20 and wall 22 cooperate to define cavity 24. Cavity 24 is sized for the receipt of a medical device component, such as one of first medical device components 26, 28, 30. As shown, medical device component 26 is an acetabular liner, medical device component 28 is a tibial articulating surface, and medical device component 30 is a tibial plate. Medical device components 26, 28, 30 may be large and/or heavy medical device components and, therefore, are positioned within cavity 24 of outer shell 12, as outer shell 12 provides the greatest amount of space for medical devices 26, 28, 30. Additionally, by placing one of medical device components 26, 28, 30 within cavity 24 of outer shell 12, the center of gravity of container system 10 is lowered, which increases the stability of container system 10. Additionally, while described and depicted herein with specific reference to medical device components 26, 28, 30, container system 10 may be utilized in conjunction with any known medical device component.

Figure 2:
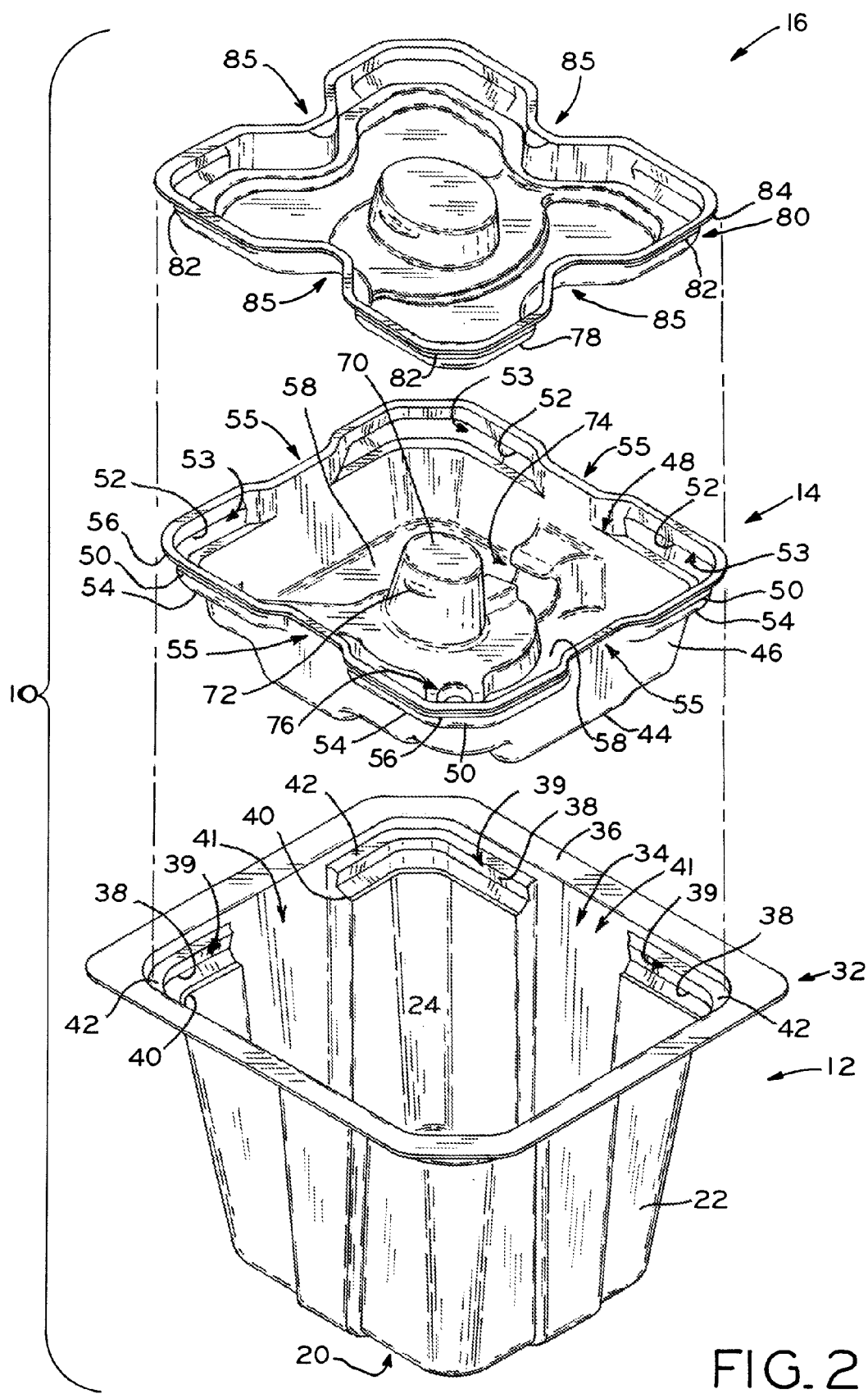
FIG. 2 is another exploded, perspective view of the container system of FIG. 1.
Figure 5:
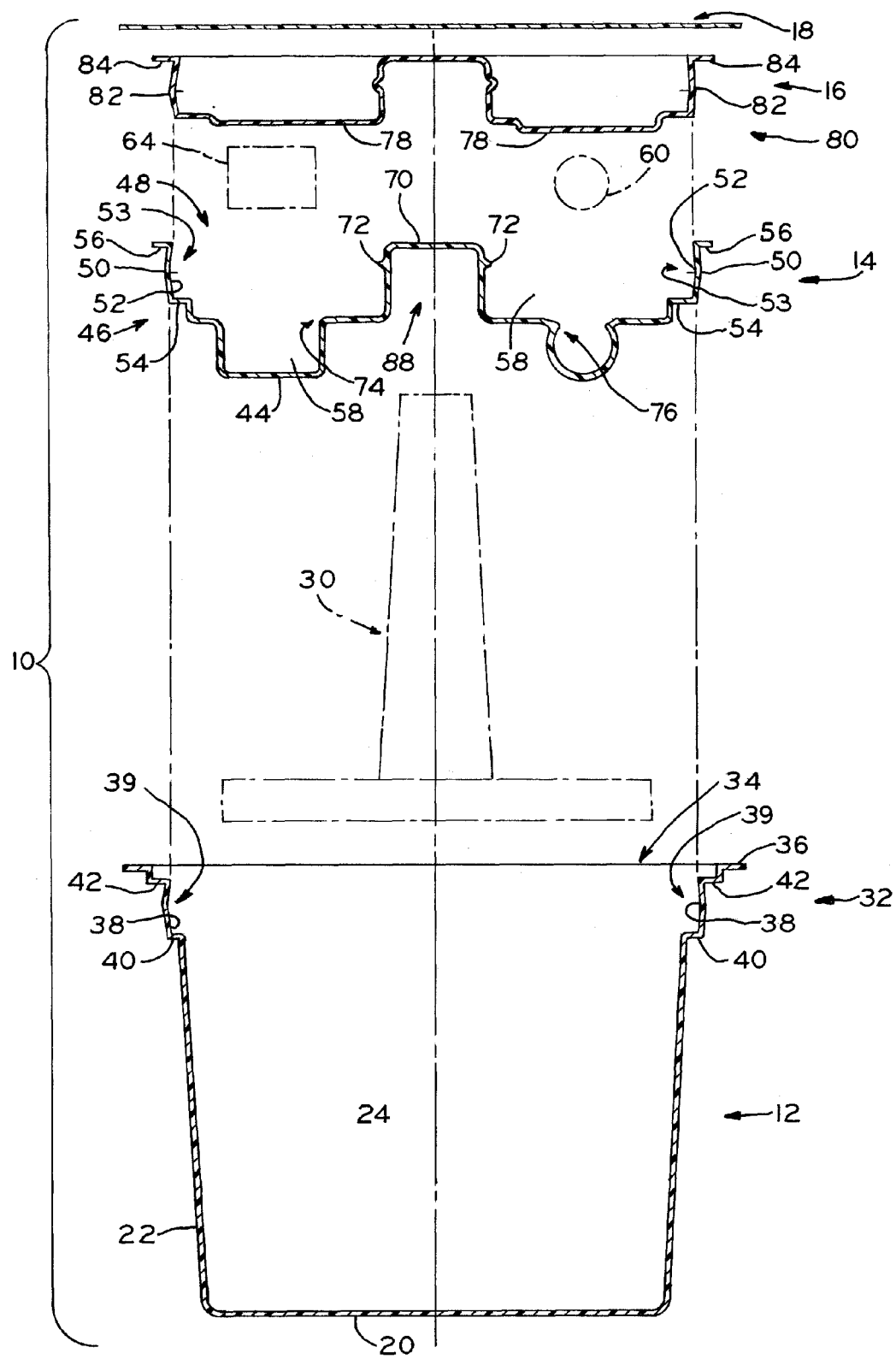
FIG. 5 is an exploded cross-sectional view of the container system of FIG. 1 taken along line 5-5 of FIG. 1 and extending between opposing corners of the container system.

Referring to FIGS. 1 and 2, wall 22 of outer shell 12 includes rim portion 32. Rim portion 32 defines opening 34 that communicates with cavity 24 of outer shell 12 and provides access to cavity 24 during insertion and removal of medical device components 26, 28, 30 from cavity 24. Rim portion 32 of outer shell 12 includes outwardly extending flange 36 and internal securement surface 38 (FIG. 5). Outwardly extending flange 36 is configured for receipt of cover 18 thereon, as described in detail below. In one exemplary embodiment, internal securement surface 38 defines groove 39 designed to receive a resiliently deformable portion of support tray 14. In one exemplary embodiment, a midpoint of internal securement surface 38 is spaced outwardly in the direction of flange 36 to define groove 39. Additionally, in one exemplary embodiment, internal securement surface 38 extends intermittently around rim portion 32. Rim portion 32 also defines internal shoulders 40, 42 of outer shell 12. In one exemplary embodiment, internal shoulders 40, 42 extend intermittently around rim portion 32. In embodiments in which internal securement surface 38 and internal shoulders 40, 42 extend intermittently around rim portion 32, recesses 41 may be formed between adjacent sections of internal securement surface 38 and internal shoulders 40, 42. In exemplary embodiments, internal securement surface 38 and internal shoulders 40, 42 are configured to engage corresponding portions of support tray 14 to secure support tray 14 within cavity 24 of outer shell 12, as described in detail below.

Referring to FIGS. 1 and 2, support tray 14 includes support floor 44 and raised wall 46 that extends upwardly from support floor 44. Support floor 44 and wall 46 cooperate to define cavity 48 of support tray 14. Wall 46 of support tray 14 defines resiliently deformable portion 50, designed for secure engagement with internal securement surface 38 of outer shell 12. In one exemplary embodiment, resiliently deformable portion 50 extends intermittently around wall 46. Additionally, resiliently deformable portion 50 of wall 46 defines internal securement surface 52 of support tray 14 that contacts a resiliently deformable portion of retention tray 16, as described below. In one exemplary embodiment, internal securement surface 52 defines groove 53. Specifically, in one embodiment, a midpoint of internal securement surface 52 is spaced in an outward direction from support floor 44 to define groove 53. In one exemplary embodiment, wall 46 also defines shoulders 54, 56 positioned adjacent internal securement surface 52 of support tray 14. In one exemplary embodiment, shoulder 54 extends intermittently around wall 46. In embodiments in which internal securement surface 52 and internal shoulder 54 extend intermittently around wall 46, recesses 55 may be formed between adjacent sections of internal securement surface 52 and internal shoulder 54. Resiliently deformable portion 50 and shoulders 54, 56 also cooperate to facilitate securement of support tray 14 to outer shell 12, as described in detail below.

Figure 3:
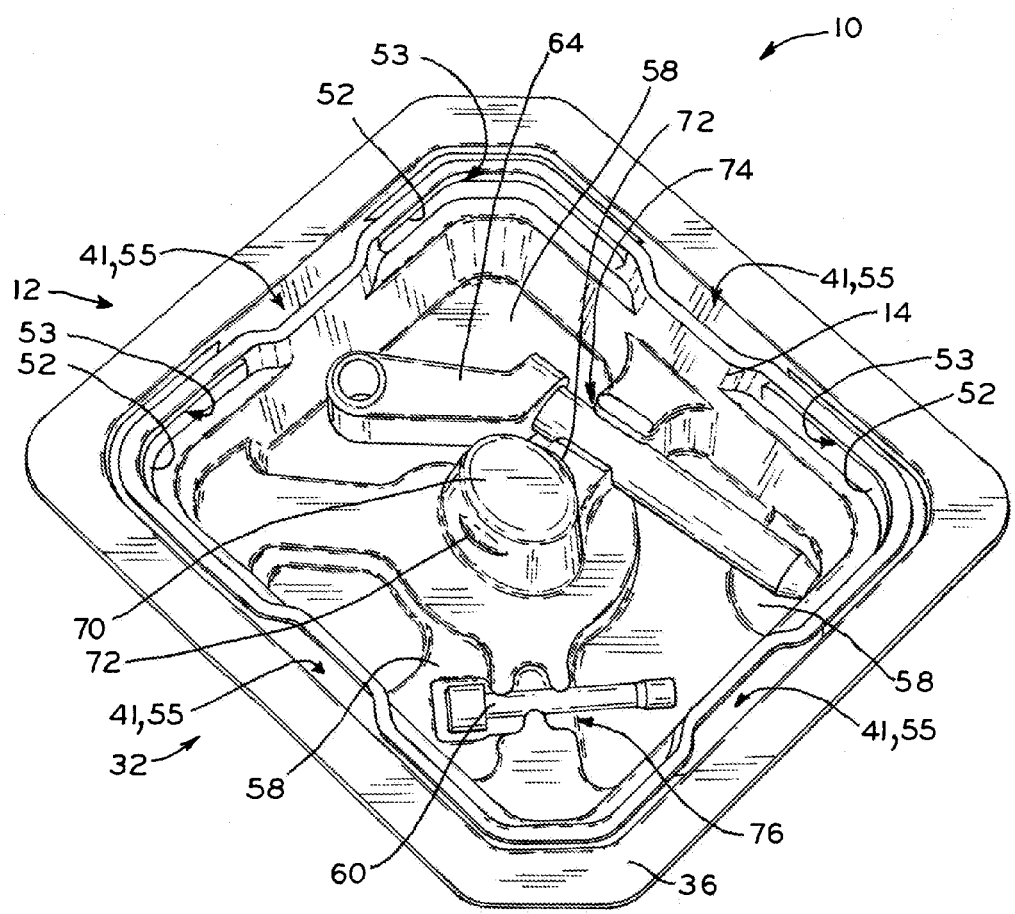
FIG. 3 is a top, perspective view of the container system of FIG. 1 depicting a support tray of the container system secured to an outer shell of the container system.

Referring to FIGS. 1 and 3, support tray 14 further includes depressions 58 that are configured for receipt of additional medical device components 60, 62, 64, 66, 68 therein. As shown in FIG. 1, medical device components 60, 62 are locking screws, medical device component 64 is a hinge post, medical device component 66 is a tibial post, and medical device component 68 is a locking ring, such as those used to secure a femoral head within an acetabular cup. By positioning a medical device component within one of depressions 58, movement of the medical device component relative to support tray 14 is restricted. Specifically, as the medical device component moves within depression 58 it may contact a wall defining depression 58. The interaction of the medical device component with the wall defining depression 58 prevents further movement of the medical device component in the direction of the wall defining depression 58. Additionally, while described and depicted herein with specific reference to medical device components 60, 62, 64, 66, 68, container system 10 may be utilized in conjunction with any known medical device component.

In one exemplary embodiment, resiliently deformable portions 74, 76 are formed within depressions 58 of support floor 44. Resiliently deformable portions 74, 76 are designed to receive and secure medical devices, such as hinge post 64 and locking screw 60, respectively, as shown in FIG. 3. By securing medical devices with resiliently deformable portions 72, 74, 76, movement of medical devices relative to support tray 14 is substantially prevented. For example, by positioning a portion of hinge post 64 adjacent resiliently deformable portion 74 and applying a force to resiliently deformable portion 74 sufficient to deform resiliently deformable portion 74, hinge post 64 may advance past resiliently deformable portion 74. Once in this position, the force is removed from resiliently deformable portion 74 and resiliently deformable portion 74 returns to its previous state, in which it extends over a portion of hinge post 64 to capture hinge post 64, as shown in FIG. 3. In this manner, hinge post 64 is substantially prevented from moving relative to support tray 14. In order to remove hinge post 64 from support tray 14, a sufficient force is applied to resiliently deformable portion 74 to cause deformation of resiliently deformable portion 74. As portion 74 is deformed, hinge post 64 is allowed to pass by portion 74 and can be removed from support tray 14.

In addition to depressions 58, support floor 44 of support tray 14 also defines projection 70. Projection 70 may be sized to receive a medical device, such as locking ring 68, thereon. For example, projection 70 may include resiliently deformable portions 72. Resiliently deformable portions 72 may be designed to allow the passage of the medical device, such as locking ring 68, over portions 72. For example, with specific reference to locking ring 68, portions 72 allow for passage of locking ring 68 by deforming inwardly in response to a downward force applied on portions 72 by locking ring 68. This deformation allows portions 72 to accommodate locking ring 68 and, once locking ring 68 has passed over portions 72, portions 72 may return to the position shown in FIG. 3. In this manner, once portions 72 return to the position shown in FIG. 3, portions 72 act to prevent locking ring 68 from being readily removed from projection 70. Thus, in order to remove locking ring 68 from projection 70, a force sufficient to deform portions 72 is applied to portions 72. Then, locking ring 68 may be advanced over portions 72 and removed from projection 70.

In another exemplary embodiment, portions 72 of projection 70 may be rigid and locking ring 68 may be sized to have an inner diameter that is sufficiently large to allow locking ring 68 to pass over portions 72 without the need to deform portions 72. In this embodiment, locking ring 68 extends around projection 70 and is retained in position by projection 70. Specifically, the interaction of the inner surface of locking ring 68 with projection 70 restricts movement of locking ring 68 relative to projection 70. In one exemplary embodiment, retention tray 16 further cooperates with projection 70 to prevent locking ring 68 from disengaging from projection 70. For example, retention tray 16 may act as a cover extending over projection 70 to limit the translation of locking ring 68 along the longitudinal axis of projection 70 and to prevent locking ring 68 from disengaging from projection 70, i.e., to prevent locking ring 68 from translating into a position in which locking ring 68 no longer extends around projection 70.

Referring to FIGS. 1 and 2, retention tray 16 is shown including tray floor 78 and raised wall 80 extending upwardly from tray floor 78. Wall 80 of retention tray 16 defines resiliently deformable portion 82 and shoulder 84. In one exemplary embodiment, resiliently deformable portion 82 and shoulder 84 extend intermittently around wall 80 of retention tray 16. In embodiments in which resiliently deformable portion 82 and shoulder 84 extend intermittently around wall 80, recesses 85 may be formed between adjacent sections of resiliently deformable portion 82 and shoulder 84. Resiliently deformable portion 82, tray floor 78, and shoulder 84 of retention tray 16 also cooperate to secure retention tray 16 to support tray 14, as described in detail below.

The final component of container system 10 is cover 18, shown in FIGS. 1 and 4. Cover 18 is designed to extend across opening 34 of outer shell 12 to prevent dirt and/or debris from entering cavity 24 of outer shell 12. In one exemplary embodiment, cover 18 is secured to flange 36 of outer shell 12 using an adhesive. In another exemplary embodiment, cover 18 is formed from a material that is impermeable to oxygen.

Figure 6:
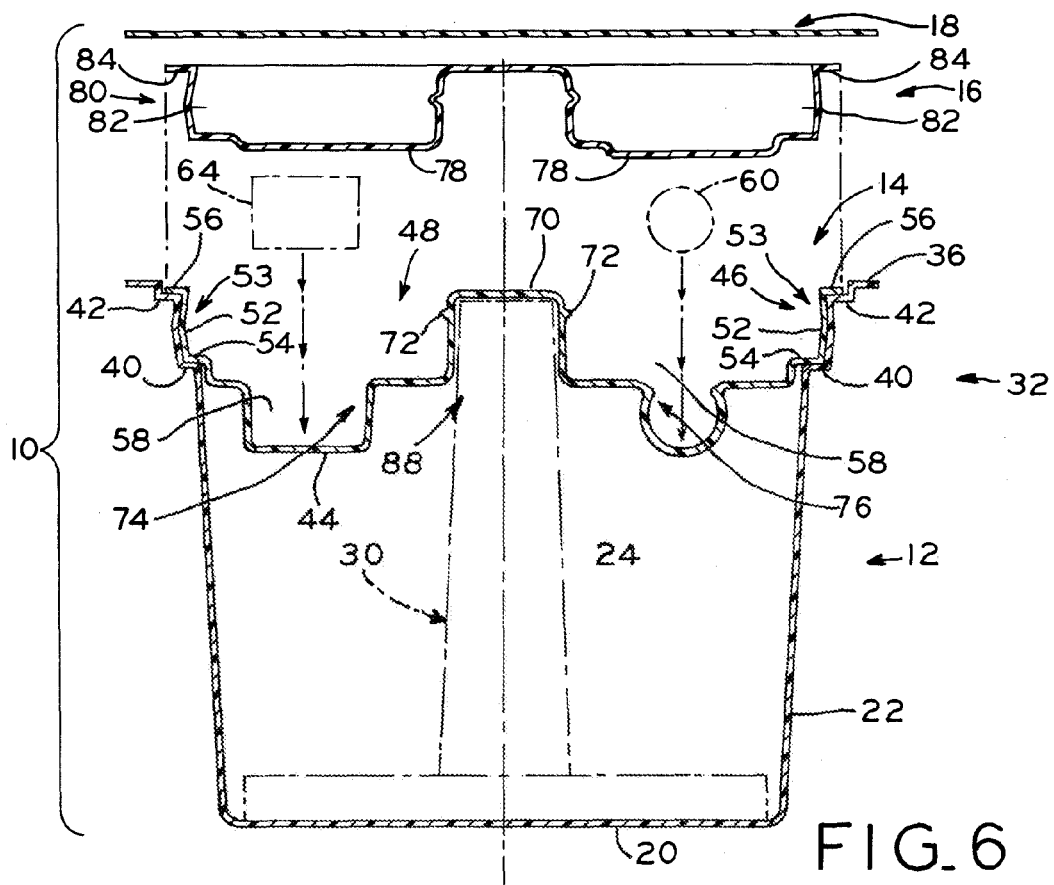
FIG. 6 is a partially exploded, cross-sectional view of the container system of FIG. 5.

Referring to FIGS. 5-7, in order to assemble container system 10, a medical device component, such as one of medical device components 26, 28, 30, is positioned within cavity 24 of outer shell 12. Once in this position, support tray 14, which is sized for receipt within cavity 24 of outer shell 12, is aligned with and inserted into outer shell 12. As support tray 14 is advanced into outer shell 12, resiliently deformable portion 50 of support tray 14 contacts internal securement surface 38 of outer shell 12. By continuing to advance support tray 14 into outer shell 12, resiliently deformable portion 50 of support tray 14 is deformed until resiliently deformable portion 50 is properly seated adjacent to internal securement surface 38 of outer shell 12.

For example, in one exemplary embodiment, once resiliently deformable portion 50 is properly seated, resiliently deformable portion 50 of support tray 14 will expand outwardly into groove 39 of internal securement surface 38 of outer shell 12. In one exemplary embodiment, portion 50 expands outwardly into groove 39 and contacts internal securement surface 38. By positioning resiliently deformable portion 50 of support tray 14 within groove 39 defined by internal securement surface 38, such that resiliently deformable portion 50 is received within groove 39, the interaction between resiliently deformable portion 50 and internal securement surface 38 provides for securement of support tray 14 to outer shell 12 with support floor 44 of support tray 14 suspended within cavity 24 of outer shell 12 at a distance spaced from shell floor 20 of outer shell 12. Thus, in order to remove support tray 14 from outer shell 12, a force sufficient to deform resiliently deformable portion 50 of support tray 14 is applied to portion 50, such as by pulling upwardly, i.e., in a direction away from shell floor 20, on support tray 14. As portion 50 deforms, resiliently deformable portion 50 passes over internal securement surface 38 of outer tray 12 to allow support tray 14 to be removed from cavity 24 of outer shell 12.

Additionally, with resiliently deformable portion 50 received within groove 39, as shown in FIG. 6, shoulders 54, 56 of support tray 14 contact corresponding shoulders 40, 42 of outer shell 12. This cooperation of shoulders 54, 56 of support tray 14 with shoulders 40, 42 of outer shell 12 provides a further mechanism for the support of support tray 14 within cavity 24 of outer shell 12. Further, in one exemplary embodiment, support floor 44 of support tray 14 is shaped to receive or otherwise contact a portion of the medical device component received within cavity 24 of outer shell 12. For example, referring to FIG. 6, support floor 44 of support tray 14 includes recess 88 that receives and/or contacts a portion of tibial plate 30. The interaction of a portion of tibial plate 30 with a portion of support floor 44 defining recess 88 restricts movement of tibial plate 30 relative to support tray 14. In this manner, support tray 14 provides an additional mechanism for the securement of tibial plate 30 in its desired position within cavity 24. Furthermore, additional medical device components may be positioned within support tray 14. For example, one or more of medical device components 60, 62, 64, 66, 68, may be secured within depressions 58 and/or by resiliently deformable portions 72, 74, 76 of support tray 14, as described in detail above.

With support tray 14 and/or one or more of medical device components 60, 62, 64, 66, 68 secured to outer shell 12, retention tray 16 may be secured to support tray 14. Referring to FIGS. 6 and 7, retention tray 16 is sized for receipt within cavities 48, 24 of support tray 14 and outer shell 12, respectively. With retention tray 16 aligned with cavity 48 of support tray 14, retention tray 16 may be advanced into cavity 48 of support tray 14. As retention tray 16 advances, resiliently deformable portion 82 of retention tray 16 contacts internal securement surface 52 of support tray 14. The interaction of resiliently deformable portion 82 with internal securement surface 52 causes deformation of resiliently deformable portion 82 of retention tray 16. As retention tray 16 is further advanced into cavity 48 of support tray 14, resiliently deformable portion 82 is further deformed until retention tray 16 is fully seated within support tray 14.

Once in this position, resiliently deformable portion 82 expands into groove 53 defined by internal securement surface 52 of support tray 14. In one exemplary embodiment, portion 82 contacts internal securement surface 52 of support tray 14. By positioning resiliently deformable portion 82 of retention tray 16 within groove 53 defined by internal securement surface 52 of support tray 14, such that resiliently deformable portion 82 is received within groove 53, the interaction between resiliently deformable portion 82 and internal securement surface 52 provides for securement of retention tray 16 to support tray 14. In addition, by positioning retention tray 16 within support tray 14 as described in detail above, retention tray 16 may act to further secure support tray 14 to outer shell 12 by providing additional biasing of resiliently deformable portion 50 of support tray 14 against internal securement surface 38 of outer shell 12. In order to remove retention tray 16 from support tray 14, a force sufficient to deform resiliently deformable portion 82 of support tray 14 is applied to portion 82, such as by pulling upwardly, i.e., in a direction away from support floor 44, on retention tray 16. As portion 82 deforms, resiliently deformable portion 82 passes over internal securement surface 52 of support tray 14 to allow retention tray 16 to be removed from cavity 48 of support tray 14.

Additionally, in one exemplary embodiment, shoulder 84 of retention tray 16 cooperates with shoulder 56 of support tray 14 and tray floor 78 of retention tray 16 cooperates with lower shoulder 54 of support tray 14 to further secure and support retention tray 16 within cavities 48, 24. Additionally, in one exemplary embodiment, shown in FIG. 7, a portion of tray floor 78 may contact one of the medical device components, such as medical device components 60, 62, 64, 66, 68, positioned within cavity 48 of support tray 14. In this manner, tray floor 78 acts to further restrict movement of a medical device component positioned within cavity 48 of support tray 14.

With outer shell 12, support tray 14, and retention tray 16 secured together, cover 18 may be secured to outwardly extending flange 36 of outer shell 12, such that cover 18 extends across and seals cavity 24 of outer shell 12. In one exemplary embodiment, cover 18 is secured to outwardly extending flange 36 to create a non-leaking union between outwardly extending flange 36 and cover 18. In one exemplary embodiment, an adhesive is applied to outwardly extending flange 36 of outer shell 12 to seal cover 18 thereto. Additionally, as indicated above, in one exemplary embodiment, cover 18 is formed from a material that is impermeable to oxygen. In this embodiment, in order to create an inert environment within container system 10, any oxygen that is present within container system 10 must be removed prior to sealing cover 18 to flange 36. For example, container system 10 may be placed under vacuum to remove any air present within container system 10.

Additionally, recesses 41, 55, 85 of outer shell 12, support tray 14, and retention tray 16, respectively, cooperate to facilitate the removal of air from container system 10 when container system 10 is placed under vacuum. Specifically, any air trapped within cavity 24 of outer shell 12 or cavity 48 in support tray 14 is allowed to pass through recesses 41, 55, 85 and exit container system 10 through opening 34 in outer shell 12. Then, container system 10 may be backfilled with nitrogen or another inert gas to create a substantially inert environment within container system 10. Specifically, the nitrogen may enter cavities 48, 24 of support tray 14 and outer shell 12, respectively, by passing through recesses 41, 55, 85 to create an inert environment within container system 10. Once an inert environment has been created within container system 10, cover 18 may be fully sealed to outwardly extending flange 36 of outer shell 12 to ensure that a sterile, inert environment is maintained within container system 10.

While this invention has been described as having an exemplary design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A container system configured for containment of a sterile medical device component, the container system comprising:
   an outer shell having a shell floor and an outer shell wall extending from said shell floor, said outer shell wall having a rim portion defining an opening in said outer shell, said rim portion having an outwardly extending flange and a first internal securement surface;
   a support tray having a support floor and a support tray wall extending from said support floor, said support floor having an upwardly projecting, first centrally positioned projection, said first centrally positioned projection having a top from which a sidewall downwardly extends, said sidewall having an exterior surface facing said support tray wall and an interior surface opposite said exterior surface, said sidewall including a resiliently deformable sidewall portion protruding from said exterior surface, said interior surface of said sidewall defining an interior space, said interior space interior of and disposed within said first centrally positioned projection, said interior space, said shell floor, and said outer shell wall cooperating to define a first cavity, said support floor and said support tray wall cooperating to define a second cavity, said support tray wall having a first resiliently deformable portion defining a second internal securement surface, said support tray sized for receipt within said first cavity, wherein, with said support tray received within said first cavity, said first resiliently deformable portion interacts with said first internal securement surface to secure said support tray to said outer shell and suspend said support floor of said support tray within said first cavity at a distance spaced from said shell floor of said outer shell; and
   a retention tray having a tray floor and a retention tray wall extending from said tray floor, said tray floor including an upwardly projecting, second centrally positioned projection having a top sized to receive and abut said top of said first centrally positioned projection of said support tray and a notch sized to receive said resiliently deformable sidewall portion of said first centrally positioned post of said support tray, said retention tray wall defining a second resiliently deformable portion, said retention tray sized for receipt within said second cavity, wherein, with said retention tray received within said second cavity, said second resiliently deformable portion interacts with said second internal securement surface to secure said retention tray to said support tray and said outer shell;
   wherein said second internal securement surface extends intermittently along said support tray wall, wherein, with said support tray positioned within said first cavity, a first vertically-facing recess is defined between said outer shell wall and said support tray wall;
   wherein said second resiliently deformable portion extends intermittently along said retention tray wall, wherein, with said retention tray positioned within said second cavity, a second vertically-facing recess is defined between said support tray wall and said retention tray wall; and
   said first recess disposed directly adjacent said second recess on an opposite side of said support tray wall, said first recess cooperating with said second recess to permit at least one of the removal of air from the container system and the insertion of inert gas into the container system.

2. The container system of claim 1, further comprising a cover secured to said outwardly extending flange of said outer shell, wherein said cover seals said first cavity.

3. The container system of claim 2, wherein said cover is formed from a material that is impermeable to oxygen.

4. The container system of claim 1, wherein said support floor of said support tray contacts a medical device component positioned within said first cavity when said support tray is received within said first cavity, said medical device component is at least one of an acetabular liner, a tibial articulating surface, and a tibial plate, whereby interaction of said medical device component with said support floor restricts movement of said medical device component.

5. The container system of claim 1, wherein said first recess is interrupted by said shell floor of said outer shell and said second recess is interrupted by said support floor of said support tray.

6. A container system configured for containment of a sterile medical device component, the container system comprising:
   an outer shell having a shell floor and an outer shell wall extending from said shell floor, said outer shell wall having a rim portion defining an opening in said outer shell, said rim portion having an outwardly extending flange and a first internal securement surface;
   a support tray having a support floor and a support tray wall extending from said support floor, said support floor having an upwardly projecting, first centrally positioned projection, said first centrally positioned projection having a top from which a sidewall downwardly extends, said sidewall having an exterior surface facing said support tray wall and an interior surface opposite said exterior surface, said sidewall including a resiliently deformable sidewall portion protruding from said exterior surface, said interior surface of said sidewall defining an interior space, said interior space interior of and disposed within said first centrally positioned projection, said interior space, said shell floor, and said outer shell wall cooperating to define a first cavity, said support floor and said support tray wall cooperating to define a second cavity, said support tray wall having a first resiliently deformable portion defining a second internal securement surface, said support tray sized for receipt within said first cavity, wherein, with said support tray received within said first cavity, said first resiliently deformable portion interacts with said first internal securement surface to secure said support tray to said outer shell and suspend said support floor of said support tray within said first cavity at a distance spaced from said shell floor of said outer shell;
   a retention tray having a tray floor and a retention tray wall extending from said tray floor, said tray floor including an upwardly projecting, second centrally positioned projection having a top sized to receive and abut said top of said first centrally positioned projection of said support tray and a notch sized to receive said resiliently deformable sidewall portion of said first centrally positioned post of said support tray, said retention tray wall defining a second resiliently deformable portion, said retention tray sized for receipt within said second cavity, wherein, with said retention tray received within said second cavity, said second resiliently deformable portion interacts with said second internal securement surface to secure said retention tray to said support tray and said outer shell; and a medical device component positioned within said second cavity, said medical device component is at least one of a locking screw, a hinge post, a tibial post, and a locking ring;

wherein said support tray defines a plurality of separately defined depressions, each depression sized for the receipt of at least one said medical device component, wherein movement of said medical device component relative to said support tray is restricted when said medical device component is received within said respective depression, a first of said plurality of separately defined depressions having a first cross-sectional shape, a second of said plurality of separately defined depressions having a second cross-sectional shape, said first cross-sectional shape different from said second cross-sectional shape.

7. The container system of claim 6, wherein said tray floor is configured to contact said medical device component when said medical device component is received within said depression, wherein interaction of said medical device component with said tray floor further restricts movement of said medical device component relative to said support tray.

8. The container system of claim 6, wherein said support tray further comprises a plurality of mutually facing pairs of resiliently deformable portions, each pair including two arms disposed in proximate relation to, and extending towards, each other, one of said arms extending from said centrally positioned projection, one other of said arms extending from said support tray wall, each pair of resiliently deformable portions sized to-receive at least a portion of said medical device component therein, wherein interaction of said medical device component with said respective pair of resiliently deformable portions restricts movement of said medical device component relative to said support tray.

9. The container system of claim 6, further comprising a cover secured to said outwardly extending flange of said outer shell, wherein said cover seals said first cavity.

10. The container system of claim 9, wherein said cover is formed from a material that is impermeable to oxygen.

11. A container system for the receipt of medical device components, the system comprising:

an outer shell having a shell floor and an outer shell wall extending from said shell floor, said outer shell wall having a rim portion defining an opening in said outer shell, said rim portion having an outwardly extending flange and an outer shell internal shoulder;

a support tray having a support floor and a support tray wall extending from said support floor, said support floor having an upwardly projecting first centrally positioned projection, said first centrally positioned projection having a top from which a sidewall downwardly extends, said sidewall having an exterior surface facing said support tray wall and an interior surface opposite said exterior surface, said sidewall including a resiliently deformable sidewall portion protruding from said exterior surface, said interior surface of said sidewall defining an interior space, said interior space interior of and disposed within said centrally positioned projection, said interior space, said shell floor, and said outer shell wall cooperating to define a first cavity, said support floor and said support tray wall cooperating to define a second cavity, said support tray wall defining a support tray shoulder, said support tray sized for receipt within said first cavity, wherein, with said support tray received within said first cavity, said support tray shoulder abuts said outer shell internal shoulder to suspend said support floor of said support tray within said first cavity at a distance spaced from said shell floor of said outer shell;

a retention tray having a tray floor and a retention tray wall extending from said tray floor, said tray floor including an upwardly projecting, second centrally positioned projection having a top sized to receive and abut said top of said first centrally positioned projection of said support tray and a notch sized to receive said resiliently deformable sidewall portion of said sidewall of said first centrally positioned post of said support tray, said retention tray wall defining a retention tray shoulder, said retention tray sized for receipt within said second cavity, wherein, with said retention tray received within said second cavity, said retention tray shoulder abuts said support tray shoulder to suspend said retention tray within said first cavity at a distance spaced from said shell floor of said outer shell; and a cover secured to said outwardly extending flange of said outer shell, wherein said cover seals said first cavity;

wherein said rim portion further comprises an internal securement surface and said support tray wall further comprises-a first resiliently deformable portion, wherein said first resiliently deformable portion contacts said internal securement surface when said support tray is received within said first cavity;

wherein said support tray wall defines a second internal securement surface and said retention tray wall further comprises a second resiliently deformable portion, wherein said second resiliently deformable portion contacts said second internal securement surface when said retention tray is received within said second cavity of said support tray; and wherein said second internal securement surface extends intermittently along said support tray wall and said second resiliently deformable portion extends intermittently along said retention tray wall, wherein, with said support tray positioned within said first cavity and said retention tray positioned within said second cavity, directly adjacent and vertically-facing first and second recesses are respectively defined between said outer shell wall and said support tray wall, and said support tray wall and said retention tray wall, said first and second recesses separated by opposite sides of said support tray wall, said first and second recesses cooperating to permit at least one of the removal of air from the container system and the insertion of inert gas into the container system.

12. The container system of claim 11, wherein said cover is formed from a material that is impermeable to oxygen.

13. The container system of claim 11, further comprising a first medical device component positioned within said first cavity that is at least one of an acetabular liner, a tibial articulating surface, and a tibial plate.

14. The container system of claim 13, wherein said support floor contacts said first medical device component positioned within said first cavity when said support tray is received within said first cavity, whereby interaction of said first medical device component with said support floor restricts movement of said first medical device component.

15. The container system of claim 11, further comprising a second medical device component positioned within said second cavity that is at least one of a locking screw, a hinge post, a tibial post, and a locking ring.

16. A container system for the receipt of medical device components, the system comprising:

an outer shell having a shell floor and an outer shell wall extending from said shell floor, said outer shell wall having a rim portion defining an opening in said outer shell, said rim portion having an outwardly extending flange and an outer shell internal shoulder;

a support tray having a support floor and a support tray wall extending from said support floor, said support floor having an upwardly projecting first centrally positioned projection, said first centrally positioned projection having a top from which a sidewall downwardly extends, said sidewall having an exterior surface facing said support tray wall and an interior surface opposite said exterior surface, said sidewall including a resiliently deformable sidewall portion protruding from said exterior surface, said interior surface of said sidewall defining an interior space, said interior space interior of and disposed within said centrally positioned projection, said interior space, said shell floor, and said outer shell wall cooperating to define a first cavity, said support floor and said support tray wall cooperating to define a second cavity, said support tray wall defining a support tray shoulder, said support tray sized for receipt within said first cavity, wherein, with said support tray received within said first cavity, said support tray shoulder abuts said outer shell internal shoulder to suspend said support floor of said support tray within said first cavity at a distance spaced from said shell floor of said outer shell;

a retention tray having a tray floor and a retention tray wall extending from said tray floor, said tray floor including an upwardly projecting, second centrally positioned projection having a top sized to receive and abut said top of said first centrally positioned projection of said support tray and a notch sized to receive said resiliently deformable sidewall portion of said sidewall of said first centrally positioned post of said support tray, said retention tray wall defining a retention tray shoulder, said retention tray sized for receipt within said second cavity, wherein, with said retention tray received within said second cavity, said retention tray shoulder abuts said support tray shoulder to suspend said retention tray within said first cavity at a distance spaced from said shell floor of said outer shell;

a cover secured to said outwardly extending flange of said outer shell, wherein said cover seals said first cavity; and a second medical device component positioned within said second cavity that is at least one of a locking screw, a hinge post, a tibial post, and a locking ring;

wherein said support tray defines a plurality of separately defined depressions, each depression sized for the receipt of said second medical device component, wherein movement of said second medical device component relative to said support tray is restricted when said second medical device component is received within said respective depression, a first of said plurality of separately defined depressions having a first cross-sectional shape, a second of said plurality of separately defined depressions having a second cross-sectional shape, said first cross-sectional shape different from said second cross-sectional shape.

17. The container system of claim 16, wherein said tray floor is configured to contact said second medical device component when said second medical device component is received within said depression, wherein interaction of said second medical device component with said tray floor further restricts movement of said second medical device component relative to said support tray.

18. The container system of claim 16, wherein said support tray further comprises a mutually facing pair of resiliently deformable portions including a first arm extending inwardly from said support tray wall, a second arm disposed proximate to, and extending towards, said first arm from said centrally positioned projection, and a gap positioned between said first and second arms, said pair of resiliently deformable portions sized to-receive at least a portion of said second medical device component within said gap, wherein interaction of said second medical device component with said pair of resiliently deformable portions restricts movement of said second medical device component relative to said support tray.

19. The container system of claim 16, wherein said cover is formed from a material that is impermeable to oxygen.

20. The container system of claim 16, further comprising a first medical device component positioned within said first cavity that is at least one of an acetabular liner, a tibial articulating surface, and a tibial plate.

21. The container system of claim 20, wherein said support floor contacts said first medical device component positioned within said first cavity when said support tray is received within said first cavity, whereby interaction of said first medical device component with said support floor restricts movement of said first medical device component.

22. A method of packaging medical device components, the method comprising the steps of:
providing a first medical device component that is at least one of an acetabular liner, a tibial articulating surface, and a tibial plate;
positioning the first medical device component in a first cavity defined by an outer shell by advancing the first medical device component through an opening defined in the outer shell;
securing a support tray within the first cavity, the support tray having a support floor with a first upwardly projecting centrally positioned projection having a top and a sidewall downwardly extending from the top, the sidewall having an interior surface substantially defining a bounded area, the first medical device at least partially positioned within the bounded area of the centrally positioned projection;
positioning a second medical device component that is at least one of a locking screw, a hinge post, a tibial post, and a locking ring within a second cavity defined by the support tray;
securing a retention tray within the second cavity, the retention tray having a tray floor including a second upwardly projecting, second centrally positioned projection having a top sized to receive and abut the top of the first centrally positioned projection of the support tray; and
securing a cover across the opening in the outer shell;
wherein the step of positioning a second medical device component within a second cavity defined by the support tray further comprises positioning the second medical device component within one of a plurality of separately defined depressions defined by the support floor of the support tray, a first of the plurality of separately defined depressions having a first cross-sectional shape, a second of the plurality of separately defined depressions having a second cross-sectional shape, the first cross-sectional shape different from the second cross-sectional shape.

23. The method of claim 22, wherein the step of securing a support tray within the first cavity further comprises securing the support tray within the first cavity to contact at least a portion of the first medical device component, whereby interaction of the first medical device component with the support tray restricts movement of the first medical device component.

24. The method of claim 22, wherein the step of securing a retention tray within the second cavity further comprises securing the retention tray within the second cavity to contact at least a portion of the second medical device component, whereby interaction of the medical device component with the retention tray restricts movement of the second medical device component.

25. The method of claim 22, further comprising, before the step of securing a cover, the step of removing air from the first cavity.

26. The method of claim 25, further comprising, after the step of removing air, the step of backfilling the first cavity with an inert gas.

* * * * *